(12) United States Patent
Lee

(10) Patent No.: US 10,111,604 B2
(45) Date of Patent: Oct. 30, 2018

(54) PORTABLE APPARATUS FOR DETECTING BREAST CANCER

(71) Applicant: Kyongho Lee, Yongin-si (KR)

(72) Inventor: Kyongho Lee, Yongin-si (KR)

(*) Notice: Subject to any disclaimer, the term of this patent is extended or adjusted under 35 U.S.C. 154(b) by 0 days.

(21) Appl. No.: 15/414,324

(22) Filed: Jan. 24, 2017

(65) Prior Publication Data

US 2017/0188878 A1 Jul. 6, 2017

Related U.S. Application Data

(63) Continuation-in-part of application No. PCT/KR2015/012619, filed on Nov. 24, 2015.

(30) Foreign Application Priority Data

Nov. 23, 2015 (KR) .......................... 10-2015-0164352

(51) Int. Cl.
*A61B 5/053* (2006.01)
*A61B 5/00* (2006.01)

(52) U.S. Cl.
CPC .......... *A61B 5/0537* (2013.01); *A61B 5/0015* (2013.01); *A61B 5/7225* (2013.01);
(Continued)

(58) Field of Classification Search
CPC ... A61B 5/0537; A61B 5/7225; A61B 5/0015; A61B 5/742; A61B 2560/0276; A61B 2560/0431
(Continued)

(56) References Cited

U.S. PATENT DOCUMENTS

| 4,328,809 A | 5/1982 | Hirschowitz et al. |
| 5,479,932 A * | 1/1996 | Higgins ............... A61B 5/0205 600/483 |

(Continued)

FOREIGN PATENT DOCUMENTS

| KR | 10-0503882 B1 | 7/2005 |
| KR | 10-0794721 B1 | 1/2008 |

(Continued)

OTHER PUBLICATIONS

International Search Report dated Aug. 22, 2016, issued by International Searching Authority in PCT/KR2015/012619 [PCT/ISA/210].

(Continued)

*Primary Examiner* — Christopher D Koharski
*Assistant Examiner* — Jonathan M Foreman
(74) *Attorney, Agent, or Firm* — Sughrue Mion, PLLC

(57) ABSTRACT

An apparatus for detecting abnormal masses such as breast cancer includes a measurement sensor configured to obtain a voltage at a first area of a first breast of a subject; a reference sensor configured to obtain a voltage at a second area of a second breast of the subject, a position of the first area corresponding to a position of the second area; and a detector, wherein the detector includes a differential amplifier configured to amplify a voltage input from the at least one of the measurement sensor and the reference sensor; an active low pass filter configured to pass a signal frequency of a low frequency band among signals transmitted from the differential amplifier; a driver amplifier configured to amplify a signal passed through the active low pass filter; and an analog-to-digital (AD) converter configured to convert the signal amplified by the driver amplifier into a digital signal.

13 Claims, 17 Drawing Sheets

(52) U.S. Cl.
CPC ...... *A61B 5/742* (2013.01); *A61B 2560/0276* (2013.01); *A61B 2560/0431* (2013.01)

(58) Field of Classification Search
USPC .......................................................... 600/547
See application file for complete search history.

(56) References Cited

U.S. PATENT DOCUMENTS

| | | | |
|---|---|---|---|
| 6,351,666 B1* | 2/2002 | Cuzick | A61B 5/04 600/547 |
| 7,853,319 B2 | 12/2010 | Davies | |
| 2002/0123694 A1* | 9/2002 | Organ | A61B 5/0536 600/547 |
| 2004/0176675 A1 | 9/2004 | Rice et al. | |
| 2005/0065418 A1 | 3/2005 | Ginor | |
| 2009/0054804 A1* | 2/2009 | Gharib | A61B 5/04001 600/554 |
| 2010/0049078 A1 | 2/2010 | Faupel | |
| 2012/0029336 A1* | 2/2012 | Terada | A61B 5/04004 600/383 |
| 2013/0218045 A1 | 8/2013 | Ironstone | |
| 2014/0128765 A1* | 5/2014 | Chetelat | A61B 5/0531 600/547 |

FOREIGN PATENT DOCUMENTS

| | | |
|---|---|---|
| KR | 10-2008-0028651 A | 4/2008 |
| KR | 10-2009-0078639 A | 7/2009 |
| KR | 10-2011-0039896 A | 4/2011 |
| KR | 10-1490811 B1 | 2/2015 |

OTHER PUBLICATIONS

Written Opinion dated Aug. 22, 2016, issued by International Searching Authority in PCT/KR2015/012619 [PCT/ISA/237].

* cited by examiner

PORTABLE APPARATUS FOR DETECTING BREAST CANCER

CROSS-REFERENCE TO RELATED APPLICATION

This is a Continuation-In-Part Application of International Application No. PCT/KR2015/012619, filed on Nov. 24, 2015, which claims priority from Korean Patent Application No. 10-2015-0164352, filed on Nov. 23, 2015, in the Korean Intellectual Property Office, the disclosures of which are incorporated herein in their entireties by reference.

BACKGROUND

1. Field

Apparatuses consistent with the exemplary embodiments relate to a portable apparatus for detecting abnormal masses of a tissue, such as breast cancer (e.g., handheld breast cancer screening device), and more specifically, to a portable apparatus capable of detecting breast cancer by setting a reference signal for a differential amplifier based on one point in a breast area instead of using a right leg driver (RLD).

2. Description of the Related Art

Breast cancer is a disease that is frequently found in females. It is possible to increase the survival rate of females with breast cancer when the breast cancer is diagnosed and treated at an early stage. However, since there is no prognosis at an early stage of breast cancer in many cases, it is not easy to confirm breast cancer. While breast cancer screening may be performed through regular health screening, it is difficult to distinguish breast cancer from a cyst or a breast tissue growth when a size of the tissue is not large. Therefore, when the size of the tissue is a certain size (e.g., about 10 mm) or greater, precise diagnosis is performed by using various diagnostic devices such as X-ray, ultrasound, and magnetic resonance imaging (MRI). In the related art, a breast cancer screening method is disclosed in Korea Patent Application Nos. 10-2009-0096934 and 10-2008-0004564. One example is to use X-rays to detect the presence of a lesion of a breast and a microcalcification lesion, but the procedure often give the subject a discomfort or pain because it is performed while the breast is pressed.

Normal somatic cells in a human body undergo a division process including a resting stage and a differentiating stage. In this case, a cell membrane is open and an ion exchange with tissues of other cells is active in a cell during the division process, and thus a potential difference between the cell membrane and basal tissue increases. In general, in a normal cell, a potential difference is about −70 mV at the resting stage and −15 mV at the differentiating stage. On the other hand, similarly to the normal cell, a cancer cell is also differentiated through a normal process. However, unlike the normal cell, the cancer cell has a differentiation time that is about half of a differentiation time of the normal cell, and the differentiation time of the cancer cell is about one hour. However, since a normal cell has a function of regulating overdifferentiation in cell tissue, the cell tissue remains in a certain shape and size. However, a cancer cell proliferates infinitely because the cancer cell does not have such a regulating function. About 1 million of cancer cells are necessary to form a cancer tissue having a diameter of about 1 cm. Among them, about 30,000 cancer cells are differentiated daily without cell death, and a potential difference of −15 to −40 mV is consistently maintained in a malignant tumor through such differentiation. When such a potential difference is detected, it is possible to distinguish tumor tissue having a small size.

In a method of the related art disclosed in Korean Patent No. 10-0794721B, a presence of an abnormal tissue and/or abnormal cellular activities are detected by measuring an amount of change in a capacitance of a biosensor according to a change in an electromagnetic field of a human body input through a biosensor and then converting a deviation from a reference value into a deviation of a frequency for measurement Also, in a method of the related art disclosed in Korean Patent No. 10-0794721B, a measurement time of about 30 minutes is necessary to obtain a balance of a biological signal when the biological signal is measured.

SUMMARY

One or more exemplary embodiments provide a portable apparatus for detecting abnormal masses of a tissue (e.g., breast cancer), capable of accurately diagnosing abnormal masses of a tissue in one breast in a short time by setting a reference signal based on a corresponding point of an area of another breast and electrically connecting a right leg driver (RLD) circuit to a differential amplifier within the apparatus, instead of directly connecting a ground circuit to a ground point (e.g., an end point of a right leg) of a human body.

According to an aspect of an exemplary embodiment, there is provided an apparatus for detecting abnormal masses of a tissue, wherein the apparatus includes a measurement sensor configured to obtain a voltage at a first area of a first breast of a subject; a reference sensor configured to obtain a voltage at a second area of a second breast of the subject, a position of the first area corresponding to a position of the second area; and a detector, wherein the detector includes a differential amplifier configured to amplify a voltage input from the at least one of the measurement sensor and the reference sensor; an active low pass filter configured to pass a signal frequency of a low frequency band among signals transmitted from the differential amplifier; a driver amplifier configured to amplify a signal passed through the active low pass filter; and an analog-to-digital (AD) converter configured to convert the signal amplified by the driver amplifier into a digital signal.

The differential amplifier may amplify a difference between voltages respectively obtained by the measurement sensor and the reference sensor.

The detector may further include an overvoltage and/or overcurrent protection circuit configured to block a leakage current from an outside.

A ground operating circuit may be electrically connected to the differential amplifier.

At least a part of the ground operating circuit may be of an open loop type.

The ground operating circuit may include an operational amplifier having two input terminals that are electrically connected to the differential amplifier and a reference voltage, respectively; a resistor electrically connected between the operational amplifier and an output voltage; a first capacitor electrically connected between the differential amplifier and the output voltage; and a second capacitor electrically connected between the operational amplifier and the output voltage.

The ground operating circuit may be electrically connected to the plurality of the differential amplifiers.

A signal frequency of the low frequency band may be about 50 Hz or less.

The apparatus may further include a controller electrically connected to the AD convertor and may store an algorithm for calculating the digital signal converted by the AD converter and determining a lesion.

The controller may further include: a sensor signal average module configured to obtain an average value of sensor signals of at least one of the measurement sensor and the reference sensor; a sensor position correction module configured to detect a signal value that exceeds an allowable range and determine whether to change a position of a sensor among the measurement sensor and the reference sensor; a sensor failure determination module configured to determine a failure in the sensor; and a lesion primary screening module configured to determine the lesion based on the average value of the sensor signals.

When a difference between An(t), which is the average value of the sensor signals input in a certain time interval (t), and a specific signal value (Dn) among a plurality of signal values input in the certain time interval (t) is equal to or greater than a specific value, the sensor signal average module may exclude the signal value in obtaining the average value of the sensor signals.

An(t), which is the average value of the sensor signals input in a certain time interval (t) may be obtained, and the sensor position correction module may be activated when a number of a sensor value (Vn) exceeding ±3.5 mV based on An(t) has a certain ratio or higher with respect to a total number (M) of the sensor signals.

An(t), which is the average value of the sensor signals input in a certain time interval (t) may be obtained, and the sensor failure checking module may be activated when a number of times a sensor value (Vn) exceeds ±3.5 mV based on An(t) has a certain ratio or higher with respect to a total number of sensing values (M) of the sensor signals.

The primary screening module may determine normality in response to the average value of the sensor signals being less than 7 mV, and determine abnormality in response to the average value being in a range from 14 mV to 20 mV.

The apparatus may further include a peripheral sensor configured to obtain a voltage around an area, of the first breast, at which the measurement sensor is positioned.

The differential amplifier may amplify a difference between voltages respectively obtained by the peripheral sensor and the reference sensor.

The reference voltage may be determined by setting one of sensor signals of at least one of the measurement sensor and the reference sensor as a reference signal.

According to an aspect of an exemplary embodiment, there is provided an apparatus for detecting abnormal masses of a tissue, wherein the apparatus includes at least one first sensor configured to obtain a voltage at a first position of a first breast of a subject; at least one second sensor configured to obtain a voltage at a second position of a second breast of the subject, the second position corresponding to the first position; a differential amplifier configured to amplify a difference between voltages respectively obtained by the at least one first sensor and the at least one second sensor; and a lesion determination controller configured to determine whether a lesion is present based on an output of the differential amplifier.

The apparatus may further include a ground operating circuit is electrically connected to the differential amplifier, wherein the ground operating circuit provides a ground by setting one of sensor signals of the at least one first sensor and the at least one second sensor as a reference signal.

According to an aspect of an exemplary embodiment, there is provided an apparatus for detecting abnormal masses of a tissue, wherein the apparatus includes a measurement sensor configured to obtain a voltage at a first area of a first breast of a subject; (n−1) number of peripheral sensors configured to obtain a voltage around the first area, n being an integer equal to or greater than two; a reference sensor configured to obtain a voltage at a second area of a second breast of the subject, a position of the first area corresponding to a position of the second area; n number of differential amplifiers configured to respectively amplify differences between the voltage obtained by the reference sensor and voltages obtained by the measurement sensor and the (n−1) number of peripheral sensors, wherein a presence of a lesion is determined based on outputs of the n number of differential amplifiers.

According to an aspect of an exemplary embodiment, there is provided a method of detecting abnormal masses of a tissue, wherein the method includes obtaining, by a measurement sensor, a voltage at a first area of a first breast of a subject; obtaining, by a reference sensor, a voltage at a second area of a second breast of the subject, a position of the first area corresponding to a position of the second area; and amplifying, by a differential amplifier, a voltage input from the at least one of the measurement sensor and the reference sensor; passing, by an active low pass filter, a signal frequency of a low frequency band among signals transmitted from the differential amplifier; amplifying, by a driver amplifier, a signal passed through the active low pass filter; and converting, by an analog-to-digital (AD) converter, the signal amplified by the driver amplifier into a digital signal.

According to an aspect of an exemplary embodiment, there is provided a method of detecting abnormal masses of a tissue, wherein the method includes obtaining, by at least one first sensor, a voltage at a first position of a first breast of a subject; obtaining, by at least one second sensor, a voltage at a second position of a second breast of the subject, the second position corresponding to the first position; amplifying, by a differential amplifier, a difference between voltages respectively obtained by the at least one first sensor and the at least one second sensor; and determining, by a lesion determination controller, whether a lesion is present based on an output of the differential amplifier.

According to an aspect of an exemplary embodiment, there is provided a method of detecting abnormal masses of a tissue, wherein the method includes: obtaining, by a measurement sensor, a voltage at a first area of a first breast of a subject; obtaining, by (n−1) number of peripheral sensors, a voltage around the first area, n being an integer equal to or greater than two; obtaining, by a reference sensor, a voltage at a second area of a second breast of the subject, a position of the first area corresponding to a position of the second area; and amplifying, by n number of differential amplifiers, respective differences between the voltage obtained by the reference sensor and voltages obtained by the measurement sensor and the (n−1) number of peripheral sensors, wherein a presence of a lesion is determined based on outputs of the n number of differential amplifiers.

BRIEF DESCRIPTION OF THE DRAWINGS

The above and/or other aspects will become apparent and more readily appreciated from the following description of exemplary embodiments, taken in conjunction with the accompanying drawings.

DETAILED DESCRIPTION

Figure 1:
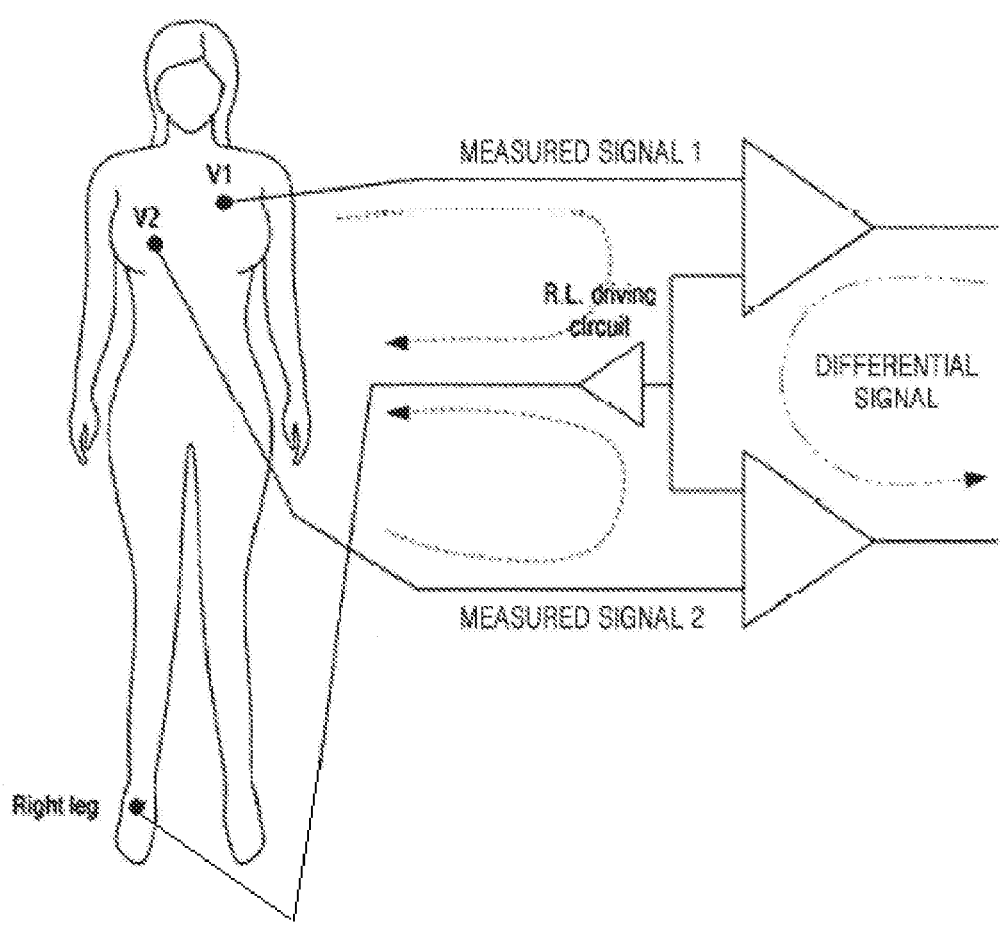
FIG. 1 is a schematic diagram showing a method of measuring a biological signal in a comparative example.

While the exemplary embodiments are susceptible to various modifications and alternative forms, specific embodiments thereof are shown in the drawings and described in detail below. However, it should be understood that there is no intention to limit the disclosure to the particular forms disclosed, and that the disclosure covers all modifications, equivalents, and alternatives falling within the spirit and scope of the disclosure.

Like numbers refer to like elements throughout the description of the figures. Sizes of elements in the drawings may be exaggerated for clarity. It should be understood that, although the terms "first," "second," etc. may be used herein to describe various elements, these elements are not limited by these terms. These terms are only used to distinguish one element from another. For example, a first element could be termed a second element, and similarly, a second element could be termed a first element, without departing from the scope of the disclosure. Elements of the invention referred to in the singular may number one or more unless clearly indicated otherwise by context.

It should be understood that the terms "comprise," "comprising," "include," and/or "including" specify the presence of stated features, numbers, steps, operations, elements, components, and/or groups thereof when used herein, but do not preclude the presence or addition of one or more other features, numbers, steps, operations, elements, components, and/or groups thereof. Also, it should be understood that, when a part such as a layer, a film, an area, or a plate is referred to as being "formed on" on another part, the part can be "formed directly" on the other part or intervening parts may be present. On the other hand, when a part such as a layer, a film, an area, or a plate is referred to as being "formed below" on another part, the part can be "formed directly below" the other part or intervening parts may be present.

Hereinafter, exemplary embodiments will be described in further detail with reference to the accompanied drawings.

The term "biological signal" herein refers to a signal generated according to an electrochemical activity of cells of nervous tissue, muscular tissue, and glandular tissue. Electrically, this "biological signal" of the cells appears when a resting potential and an action potential are generated. A breast cancer cell and a normal cell are different for various reasons, and have a difference in electrochemical aspects. When a normal cell is in a resting stage after cell division is completed, a potential difference between a cell membrane and a basilar membrane is maintained at a certain value. A living cell maintains concentrations of ions in the cell at constant values by exchanging ions through a cell wall according to energy activity. Concentrations of ions are changed between an inside and an outside of the cell wall, and a potential difference of a constant level of −70 mV is maintained between the cell and a cell fluid. The potential difference is maintained only in the resting stage. When the cell starts division activity, the cell membrane is deformed, and the potential difference is reduced to about −15 mV to 0 mV. When a normal cell has completed cell division, a potential difference of the normal cell is restored to an original value thereof. However, unlike a normal cell, in a cancer cell, an active ion exchange does not occur in cancer tissue centered at the cell membrane, and the cancer cell has a biological signal of −40 mV to −15 mV due to overdifferentiation.

FIG. 1 is a schematic diagram showing a method of measuring a biological signal in a comparative example.

Referring to FIG. 1, in a medical device for measuring a biological signal in a comparative example, a unipolar method and a bipolar method can be selectively used in order to use a differential amplifier according to an application of the signal. The bipolar method is exemplarily used in FIG. 1. A measured signal 1 refers to a difference value (V1−Vref) between a value measured at an area V1 and a reference signal at a right leg (or right foot, or an end point of a right leg). A measured signal 2 refers to a difference value (V2−Vref) between a value measured at an area V2 and a reference signal at the right leg. In this case, a differential signal value is a difference value (V1−V2) between the measured signal 1 and the measured signal 2. The bipolar method is more effective than the unipolar method in consideration of a resolution of a signal. However, when the bipolar method is used, there is a problem in that noise is frequently generated.

Also, when the unipolar method or the bipolar method is used, a right foot is used as a reference signal with respect to a signal to be measured. The right foot is a ground point of a human body when the human body and a measurement device are connected. A hand area can be used instead of the foot area. The ground point is a point connected to a reference signal of a device when a signal of the human body is measured. When a signal measured at the human body is transmitted to an input end of the measurement device, a return path through which remaining energy other than the signal to be transmitted is returned to the human body needs to be formed. The ground under the right leg serves as a relay between measured signals. Therefore, it is possible to decrease common mode interference that occurs in a signal transmission path. However, there is a problem in that, when the right leg as a reference signal is located farther from a measurement area, an impedance between two points increases, and a time required for the reference signal of the right leg to be in a steady state increases. This is because an impedance value in a homogeneous conductor is proportional to a length of the conductor. Also, when the number of measured signal groups increases, a subtle performance difference caused by tolerance of each measurement device further increases a time required for the reference signal of the right leg to be in the steady state, which results in problems in which a time required for stabilizing the signal increases and such an increased time causes thermal noise due to an increased temperature of the device so that it is difficult to measure the signal accurately.

Figure 2:
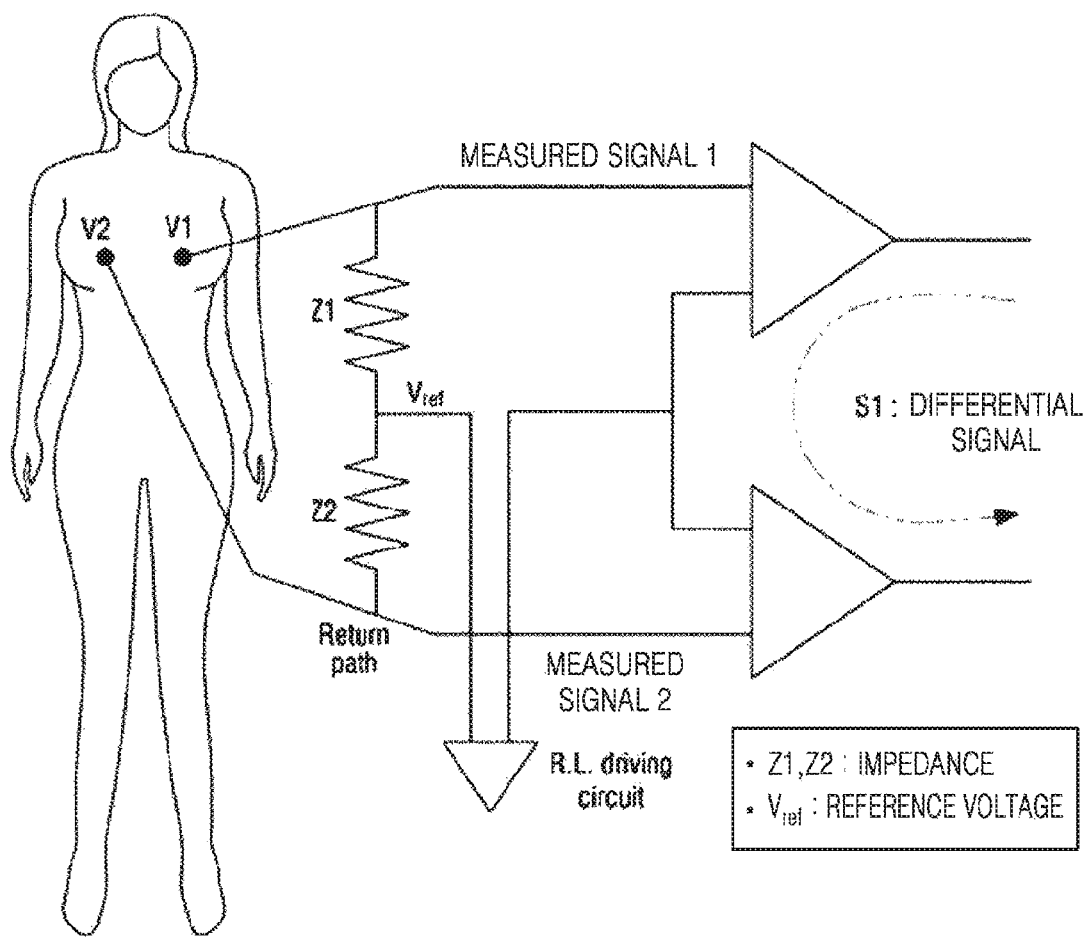
FIG. 2 is a schematic diagram showing a measurement method used by a portable breast cancer detection apparatus according to an exemplary embodiment.

FIG. 2 is a schematic diagram showing a measurement method in a portable breast cancer detection apparatus without a ground position of a right leg reference signal according to an exemplary embodiment.

Compared with FIG. 1, in an exemplary embodiment as shown in FIG. 2, in order to obtain rapid stabilization of a signal, a measured signal is set as a reference signal without setting a right leg ground position. Therefore, it is not necessary to separately set a ground position at a human body, and thus measurement positions of V1 and V2 may become closer, to decrease an impedance. Accordingly, a signal can be further rapidly stabilized.

Instead of using a right leg operating circuit in FIG. 1, an exemplary right leg operating circuit in the portable breast cancer detection apparatus in FIG. 2 is connected to a reference voltage Vref for direct stabilization. In this case, a direct voltage (DC) voltage is used as the reference voltage to provide a voltage that serves as a reference for the circuit. Also, according to an exemplary embodiment, the reference voltage may be lower than a bias voltage that is used in an amplifier circuit, and a voltage capable of providing a resolution to perform analog/digital (A/D) conversion may be provided.

When the circuit as shown in FIG. 2 is used, stabilization can be achieved at the same time as a time at which a power source of a screening device is turned on. Therefore, it is possible to measure a flow of a measured signal rapidly and accurately. As an example, a protection circuit having a symmetrical structure in which Z1 and Z2, which indicate impedances, have the same value and an impedance value is 200 Kohm or more may be provided, but the exemplary embodiments are not limited thereto. An output of a right leg driving circuit is not separately connected and remains in a floating state.

Figure 3:
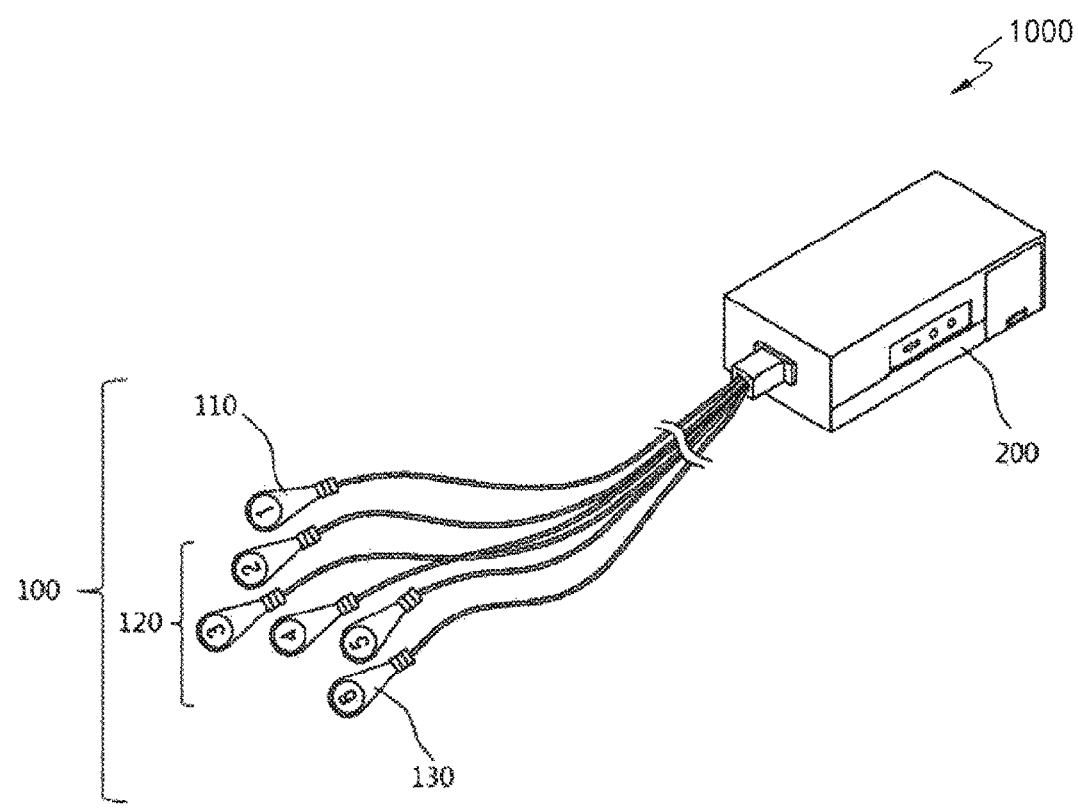
FIG. 3 is an exemplary diagram showing a portable breast cancer detection apparatus and a sensor unit according to an exemplary embodiment.
Figure 4:
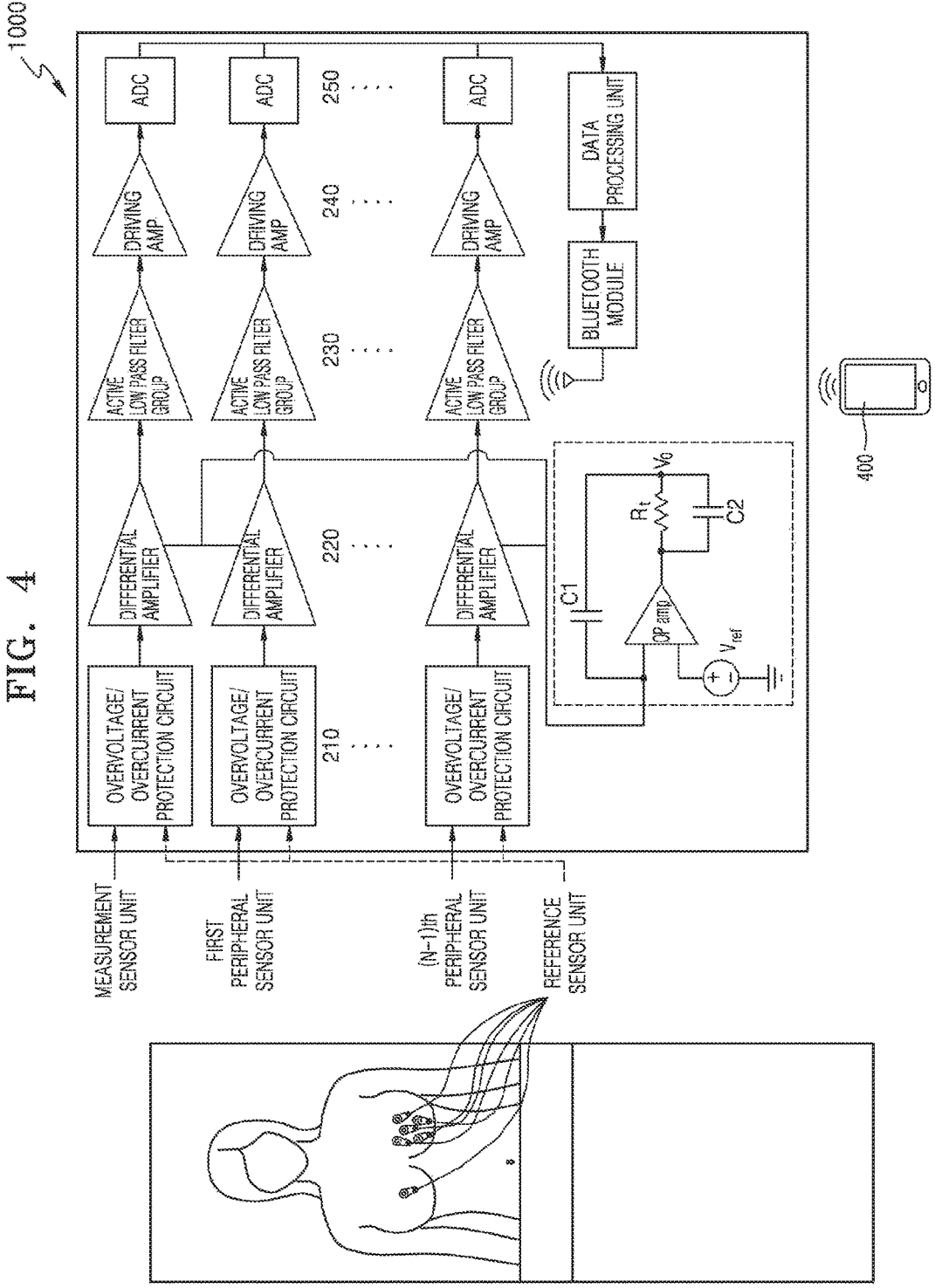
FIG. 4 is an exemplary diagram showing an example of using a portable breast cancer detection apparatus and a sensor unit according to an exemplary embodiment.

FIG. 3 is an exemplary diagram showing a portable breast cancer detection apparatus and a sensor unit according to an exemplary embodiment. FIG. 4 is an exemplary diagram showing an example of using a portable breast cancer detection apparatus and a sensor unit according to an exemplary embodiment.

Figure 5:
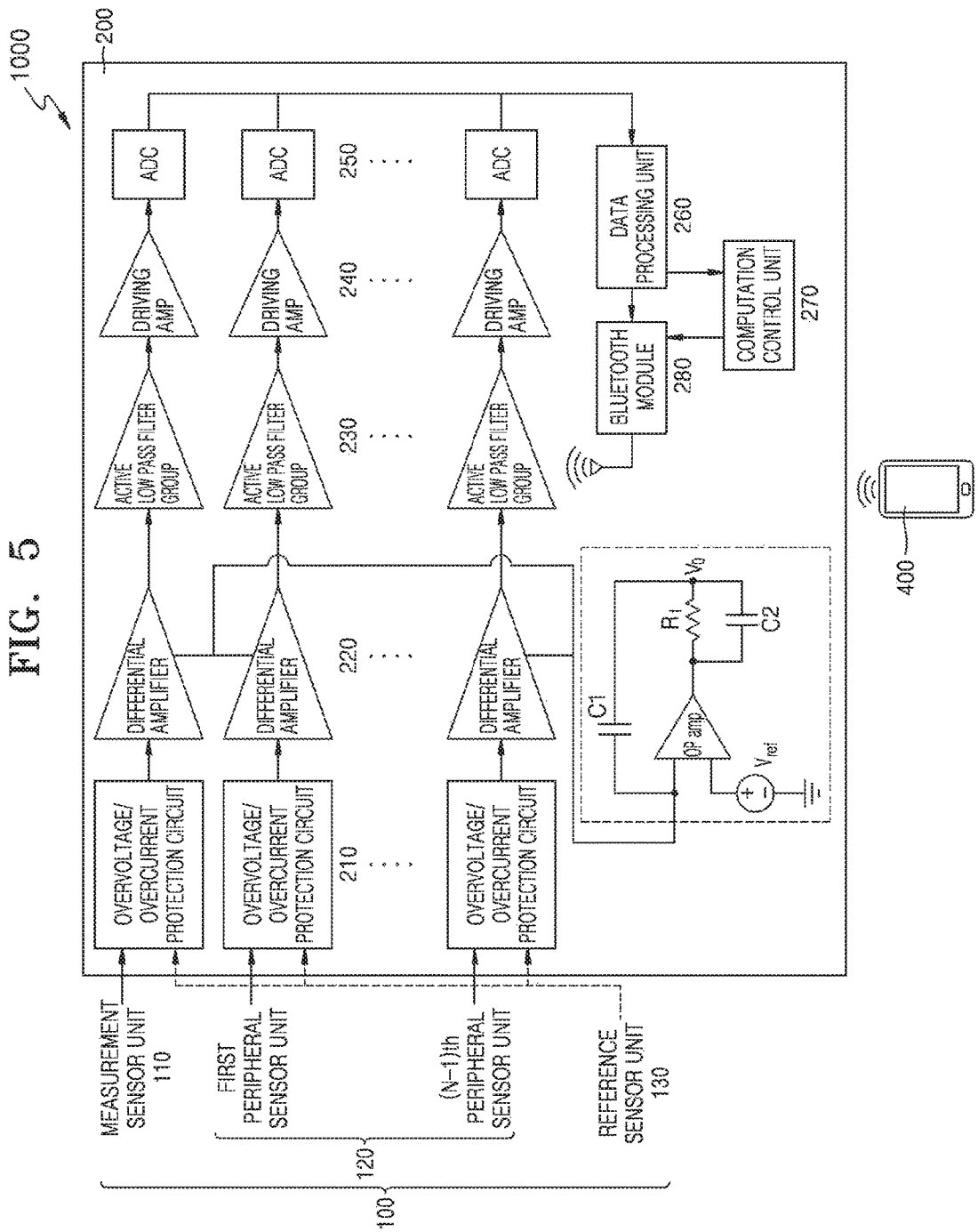
FIG. 5 is a configuration diagram showing components of a portable breast cancer detection apparatus according to an exemplary embodiment.

FIG. 5 is a configuration diagram showing components of a portable breast cancer detection apparatus according to an exemplary embodiment.

Figure 6:
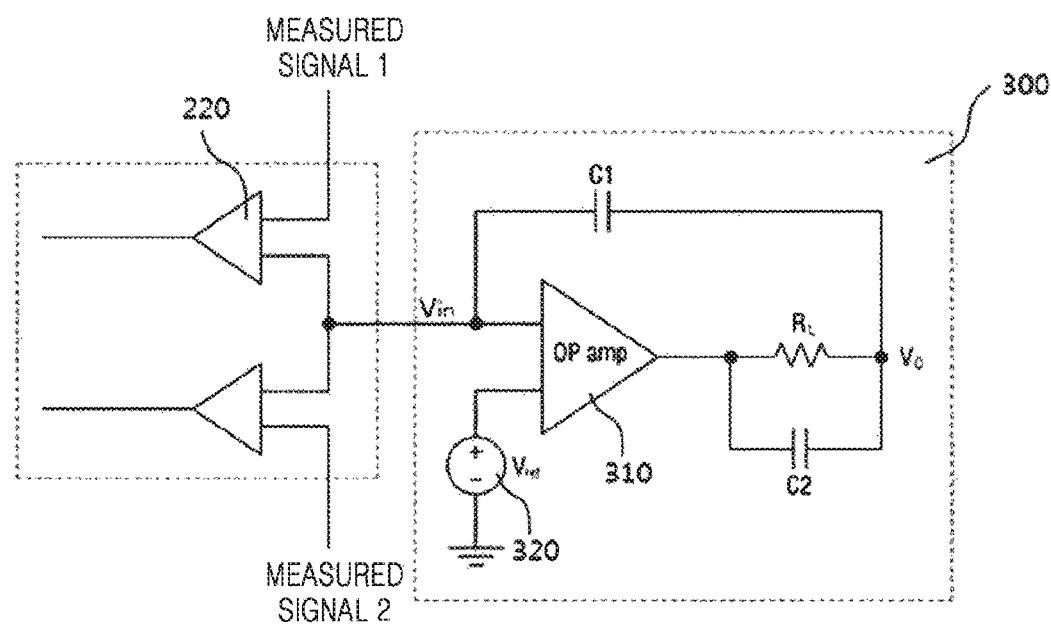
FIG. 6 is a detailed circuit diagram showing a first amplifier and a ground operating circuit that is electrically connected thereto in a portable breast cancer detection apparatus according to an exemplary embodiment.

FIG. 6 is a detailed circuit diagram showing a first amplifier and a ground operating circuit that is electrically connected thereto in a portable breast cancer detection apparatus according to an exemplary embodiment.

Figure 7:
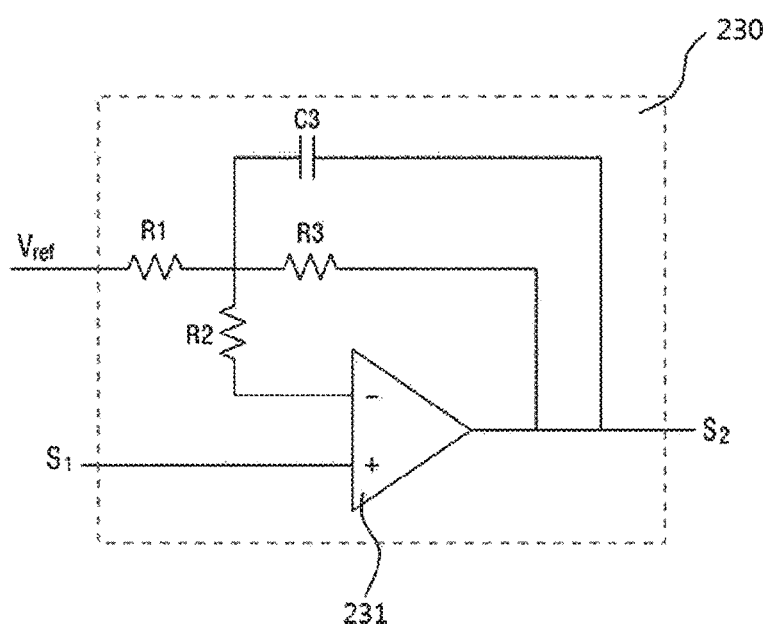
FIG. 7 is a detailed circuit diagram showing an active filter in a portable breast cancer detection apparatus according to an exemplary embodiment.

FIG. 7 is a detailed circuit diagram showing an active filter in a portable breast cancer detection apparatus according to an exemplary embodiment.

Figure 8:
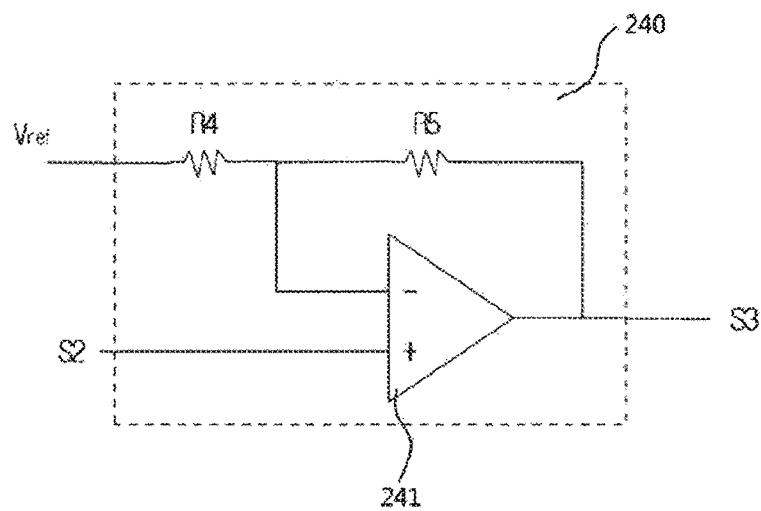
FIG. 8 is a detailed circuit diagram showing a second amplifier in a portable breast cancer detection apparatus according to an exemplary embodiment.

FIG. 8 is a detailed circuit diagram showing a second amplifier in a portable breast cancer detection apparatus according to an exemplary embodiment.

As shown in FIG. 3 and FIG. 4, a portable breast cancer detection apparatus 1000 is a portable screening device, and may include a sensor unit 100 and a detector 200. The sensor unit may have a structure in the form of a cable to which a screening sensor is attached. The screening sensor of the sensor unit 100 may include a hydrogel having high impedance and metallic electrodes having high conductivity. Each of the metallic electrodes is electrically connected to a conductive cable and may transmit an electrical signal to the breast cancer screening device. An exemplary material of a sensor includes an electrode having Ag/AgCl plating and/or a half cell characteristic equivalent thereto. A hydrogel is a high impedance gel that connects an electrode and a human body and suppresses an occurrence of an overcurrent.

The sensor unit 100 connected to the portable breast cancer detecting apparatus 1000 may include a measurement sensor unit (or a measurement sensor) 110, a plurality of peripheral sensor units (or a plurality of peripheral sensors) 120, and a reference sensor unit (or a reference sensor) 130. In a measurement area inside the sensor unit 100, a voltage is generated in the sensor unit 100 when charging is performed due to an electromagnetic induction phenomenon according to an action potential of inner skin cells of a subject. The sensor unit 100 may detect a precancerous change and an adjacent malignant tumor at an early stage using a current-passing electrode. When the above electrode is used, structural information and functional information of a screening target tissue may be provided based on a measured value of a potential difference in a specific range frequency, and corresponding depth and local anatomical information may be provided. A direct current potential difference or an alternating current potential difference may be measured in abnormal tissue or cancerous tissue to confirm the presence of abnormal precancerous cell tissue or cancerous cell tissue.

Figure 12:
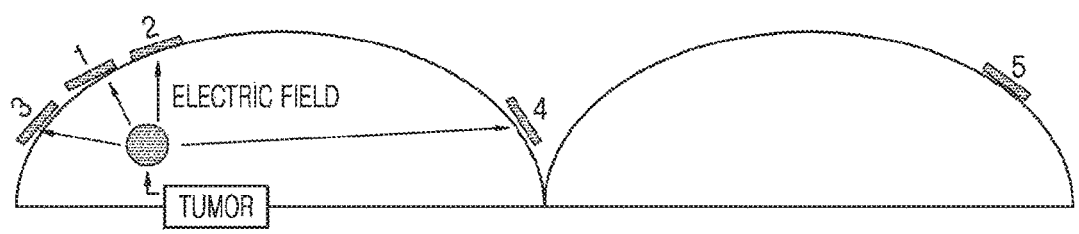
FIGS. 12 and 13 are schematic diagrams showing processes performed by a plurality of sensor units according to an exemplary embodiment to determine a relative position with respect to a position of a malignant tumor and measure a biological signal based thereon.

The measurement sensor unit 110 of the sensor unit 100 is a sensor that is attached to one breast of the subject, and is a sensor that is attached to an area of the subject to check whether the area has a tumor and measure a biological signal of the subject. The reference sensor unit 130 is a sensor that is attached to the other breast of the subject at a position corresponding to that of the one breast to which the measurement sensor unit is attached to the subject and measures a biological signal of the subject. Here, for example, corresponding positions are a position to be measured on the left breast and a position to be measured on the right breast. Here, the term "positions corresponding to each other" refers to the same positions in the left and right breasts with respect to a center of the left breast and a center of the right breast. That is, two corresponding points in the left breast and the right breast have the same angle and distance from a center point of the left breast and a center point of the right breast, respectively. For example, as shown in FIG. 12, a location of a fourth sensor 4 in the left breast and a location of a fifth sensor 5 in the right breast correspond to each other and correspond to the same positions in both breasts.

The measurement sensor unit 110 and the reference sensor unit 130 measure a biological signal at a first position to be measured and a biological signal value at a second position that corresponds to the first position, and measure a difference between voltage values at the first and second positions. It is rare that tumors appear in breast cells at the same positions in both breasts. As discussed above, the same positions in both breasts refer to two corresponding points in the left and right breasts.

Accordingly, when there is substantially no difference between voltages measured at specific positions of both breasts, it indicates that cells at the positions are highly unlikely to be tumor cells. In such cases, it is interpreted that the voltages at specific positions of both breasts are generated by normal cells.

On the other hand, when the measurement sensor unit 110 is attached to a part which has breast cancer or a breast tumor, the reference sensor unit 130 is attached at a position corresponding to that part and two biological signal values are measured, it is very likely that the two values will not match. Based on the above characteristics (e.g., similarity or difference between two values measured from corresponding positions of breasts), components included in the portable breast cancer detecting apparatus 1000 may easily determine whether a tumor is benign or malignant.

A plurality of peripheral sensor units 120 may be arranged around the measurement sensor unit 110 to obtain higher accuracy. At least one or the plurality of peripheral sensor units 120 are attached around the measurement sensor unit 110 that is attached to the one breast to be measured and a biological signal value at the attachment area is measured to correct the biological signal value measured by the measurement sensor unit 110 to be more accurate.

As shown in FIG. 5, one exemplary portable breast cancer detecting apparatus 1000 includes an overvoltage/overcurrent protection circuit 210, a first amplifier, a ground operating circuit 300, an active filter, a second amplifier, and an AD converter 250. The portable breast cancer detecting apparatus 1000 may be electrically connected to the sensor unit 100.

The portable breast cancer detecting apparatus 1000 measures a biological signal of a subject using the sensor unit 100 of a breast cancer diagnostic screening device. The portable breast cancer detecting apparatus 1000 may be connected to the sensor unit 100 configured to measure a biological signal around a breast of the subject.

The overvoltage/overcurrent protection circuit 210 is a component that is attached to one side of the chest (or breast) of the subject away from the sensor unit 100 attached to a measurement area of a breast, and protects the device from causing an error, for example, an error due to static electricity, when a current is measured by the sensor unit 100, and also prevents an external high voltage/current that may be generated in the screening device from flowing into a human body. In general, the overvoltage/overcurrent protection circuit 210 may include components that satisfy standards of electrical safety. A plurality of overvoltage/overcurrent protection circuits 210 may be provided in correspondence to the measurement sensor unit 110, the plurality of peripheral sensor units 120, and the reference sensor unit 130 so that biological signals measured by the measurement sensor unit 110, the plurality of peripheral sensor units 120 and the reference sensor unit 130 primarily pass through the overvoltage/overcurrent protection circuits 210 when voltages corresponding to the biological signals are applied to an inside of a circuit of the portable breast cancer detecting apparatus 1000.

The first amplifier amplifies a voltage signal that is input through the sensor unit 100. Generally, since a potential difference generated according to activity of cell tissue has a low level that is several mV, a level of a voltage may be amplified to obtain a meaningful measurement result.

One exemplary embodiment of the first amplifier may include a differential amplifier 220. The differential amplifier 220 is a functional block of an integrated circuit (IC) and is used as an operational amplifier and a comparator IC input end. The differential amplifier 220 includes two input terminals and two output terminals and amplifies a difference between two input signals. The differential amplifier 220 may be implemented by a BJT or a MOSFET, and may be configured as an emitter-coupled differential source, an active load, and various combinations thereof in the form of a block.

Two signals input to the differential amplifier 220 include a biological signal value that is measured by the measurement sensor unit 110 attached to one breast and a biological signal value that is measured by the reference sensor unit 130 attached at a position corresponding thereto. As an example, when levels of the two biological signals applied to the two input terminals of the differential amplifier 220 are the same or have substantially the same value, a difference between the two voltages is measured as being 0 or a value close to 0. Since the difference between two voltages is zero or very small, a differentially amplified value is measured as being a very small value.

On the other hand, when the two levels of the biological signals applied to the two input terminals of the differential amplifier 220 are different from each other, there is a difference between the two voltages. When the difference is amplified, it becomes greater than a level obtained by amplifying the difference between the two voltages that is zero or is measured as being a very small value.

Also, sources of the biological signals applied to the two input terminals may be biological signals that are measured by the plurality of peripheral sensor units 120 instead of the measurement sensor unit 110, and a biological signal that is measured by the reference sensor unit 130. The plurality of peripheral sensor units 120 are attached around one breast to which the measurement sensor unit 110 is attached, and when the plurality of peripheral sensor units 120 are attached to a normal cell, a value measured by the reference sensor unit 130 and values measured by the plurality of peripheral sensor units 120 are the same or substantially the same, and thus may be measured as relatively small values even though they are amplified by the differential amplifier 220. On the other hand, when the plurality of peripheral sensor units 120 are arranged on areas which have breast cancer cells or tumor cells, there is a difference between values of the two inputs applied to the differential amplifier 220. Since the above operation is similar to the principle described in the measurement sensor unit 110, additional description thereof will be omitted.

The portable breast cancer detecting apparatus 1000 according to an exemplary embodiment may include one differential amplifier 220, or include a plurality of differential amplifiers 220. The plurality of differential amplifiers 220 amplify potential differences between the measurement sensor unit 110 and the reference sensor unit 130 and the plurality of peripheral sensor units 120 and the reference sensor unit 130 and transmit a corresponding signal to the active filter.

As shown in FIG. 6, the ground operating circuit 300 of the portable breast cancer detecting apparatus 1000 according to an exemplary embodiment may include an OP amp 310, a reference voltage Vref 320, capacitors C1 and C2, and a resistance RL. The OP amp 310 refers to an operational amplifier. One exemplary OP amp 310 includes two input terminals that are respectively electrically connected to the differential amplifier 220 and the reference voltage 320. A right leg signal output end is not separately electrically connected and an open loop is formed to rapidly stabilize a plurality of biological signals measured by the portable breast cancer detecting apparatus 1000. In an open loop state, the reference voltage 320 is not directly connected to the first amplifier, more specifically, to the differential amplifier 220, and is connected to the OP amp 310. The OP amp 310 may restrict a flow of a current and block a change in the reference voltage 320 for protection.

One example of the portable breast cancer detecting apparatus 1000 may include the active filter. The active filter is a filter circuit that includes an active element, C, and R and uses an OP amp, and may be widely used in a low frequency range (e.g., about 10 kHz or less). The active filter removes an insertion loss in the filter circuit and also appropriately amplifies a signal.

Types of active filters include a low pass filter (LPF), a high pass filter, a band pass filter, and a band stop filter. The LPF allows a signal having a cutoff frequency of a filter or less to pass therethrough. Unlike the LPF, the high pass filter allows a signal having a cutoff frequency of the filter or higher to pass therethrough. The band pass filter is a filter that allows signals between a lower limit frequency and an upper limit frequency to pass therethrough. The band stop filter blocks only a signal of a specific range of frequency and allows other frequency signals to pass therethrough.

The active filter used in the portable breast cancer detecting apparatus 1000 may be a LPF (or an active LPF) 230. The LPF 230 is provided to remove high frequency noise. Among biological signals of 50 Hz generated in a bioelectromagnetic field, a biological signal associated with carcinogenesis has a low frequency band. Therefore, a LPF configured to block a frequency band of a corresponding band or higher may be used so that a frequency band of 50 Hz or higher is filtered. Therefore, a pass band ripple of the active LPF 230 of the portable breast cancer detecting apparatus 1000 may be regulated to 0.5 dB or less, and a 3 dB cut off frequency may be about 50 Hz. Although a signal having a frequency greater than 50 Hz may pass through the active LPF 230, the signal having a frequency greater than 50 Hz has a larger amount of attenuation than that of a frequency of less than 50 Hz, and thus the signal having a frequency greater than 50 Hz is difficult to substantially influence a signal system.

As shown in FIG. 7, a circuit of the active LPF 230 may include a reference voltage Vref, a capacitor C1, resistances R1, R2, and R3, and an active LPF element 231. The active LPF element 231 may compensate for a loss of signal power generated in a passive LPS and also amplify a signal that passes through the LPF 230. An output signal input to S1 from the differential amplifier 220 may be amplified as an output signal of S2 through the active LPF element 231, and an amplification ratio thereof is theoretically S2/S1=(R1+R3)/R1. A capacitor C3 may be used to regulate a value of a frequency signal that passes through the active LPF element 231. A pass frequency (f) is $1/(R3 \times C3)$. Resistances and capacitors respectively having various R3 values and C3 values may be used in combination to regulate a frequency to 50 Hz.

Also, in an exemplary embodiment, the LPF element 231 used in the portable breast cancer detecting apparatus 1000 may be a Chebyshev type equally ripple filter. Alternatively, Butterworth type, Bessel/Gaussian type, and elliptic type active filters may be used. However a Butterworth filter has a problem in that it is difficult to obtain a significant attenuation characteristic in an attenuation band even though the Butterworth filter has a flat characteristic in a pass band.

A Bessel filter has a problem similar to the Butterworth filter in that it is difficult to obtain a significant attenuation characteristic. A Chebyshev type filter, which is useful when a return loss ripple and passband attenuation are not important, is appropriately used as the active filter of the portable breast cancer detecting apparatus 1000. The Chebyshev type filter has a characteristic in that a low pass response has attenuation due to a ripple in a block frequency and the same attenuation ripple occurs in a pass band, and a significant attenuation characteristic is obtained in an attenuation band.

The second amplifier is used to amplify only a voltage signal in a low frequency band of 50 Hz or less that has passed the active filter. In an exemplary embodiment, the second amplifier is a driver amplifier 240. A main function of the driver amplifier 240 is to electrically separate an analog end that mainly amplifies a biological signal and a digital end starting from an AD converter and stably transmit the amplified biological signal to the digital end. One exemplary driver amplifier 240 may have has a common-mode rejection ratio (CMRR) of at least 60 dB within 50 Hz, and gains having a linear characteristic from 1 to 100 in 0 to 50 Hz bands may be used in a linear characteristic of a large signal gain ratio and a linear characteristic of a small signal gain ratio.

As shown in FIG. 8, a driver amplifier element 241 serves as a link that connects an analog end that amplifies a biological signal and a data end that converts the signal into a digital signal for processing data. The driver amplifier element 241 electrically separates an input signal S2 and an output signal S3. An amplification ratio (S3/S2), which is a ratio between the input signal S2 and the output signal S3, may be regulated by resistance values R4 and R5, and the ratio is (R4+R5)/R4. One exemplary driver amplifier may perform regulation so that a signal is always transmitted from an input end to an output end and there is no influence on the input signal S2 even when the output signal S3 is changed without being linked to the input signal S2.

A range of a biological signal to be measured is −7 mV to 20 mV, and the measured value is amplified to 0 to 4 V, which is an operating voltage of an AD converter, to correspond to the range of the biological signal. As a result, when the signal has passed through various amplification modules of the screening device, an amplification ratio of a biological analog signal may be about 200. The operating voltage described in an exemplary embodiment is only an example. The operating voltage of the AD converter is not limited to 4 V, and may be greater than or less than 4 V and support a conversion resolution of the AD converter. A resolution used in the exemplary embodiment is 1024, and a resolution of about 4 mV/bit is provided. In such a configuration, a biological signal input greater than 20 mV and −7 mV or less is saturated at an amplification end and is output as a signal of 0 V to 4 V, which refer to a lower limit value and an upper limit value. Such conversion details are summarized in the following Table 1.

TABLE 1

| Differential signal Level (mV) | S3 signal level (V) | AD converter binary number | AD converter hexadecimal number |
|---|---|---|---|
| −7 | 0 | 0000000000 | 000 |
| 0 | 1 | 0100000000 | 100 |
| 7 | 2 | 1000000000 | 200 |
| 14 | 3 | 1100000000 | 300 |
| 20 | 4 | 1111111111 | 3FF |

All amplification processes may be designed to obtain an amplification ratio of about 200 in a plurality of signals of 50 Hz or less. Since signal distortion may occur due to a linear characteristic of a device when a specific amplification process is performed at the amplification ratio of 200, multiple amplification processes may be performed. However, when there are excessive number of amplification processes, a signal-to-noise ratio may be deteriorated due to thermal noise. Thus, providing efficient amplification step is desirable. In an exemplary embodiment, three amplification processes may be used, and amplification ratios of the differential amplifier to the driver amplifier are as follows.

Differential amplifier: 15
Active low pass filter: 13.4
Driver amplifier: 1

An overall amplification ratio obtained through the above modules is about 201.00. According to a characteristic and a tolerance of a device that is actually used, an amplification ratio is designed to have 201 ± an error of 2%.

The AD converter 250 converts an analog voltage signal transmitted from the second amplifier into digital data that can be processed in a data processing unit. According to an exemplary embodiment, 10-bit analog digital conversion is performed in the AD converter 250, and a conversion rate may be 200 times/sec or less for each channel. The digital data converted in the AD converter 250 is transmitted to a data processing unit 260. Alternatively, the AD converter 250 and the data processing unit 260 may be integrated.

Referring again to FIG. 8, a signal S3 output from the second amplifier may be transmitted to the AD converter 250 and converted into raw digital data having a resolution of 10 bits. For example, the signal may be converted into a hexadecimal number and converted into a value of 0 to 3FF. The signal S3 is converted by the AD converter 250 according to a voltage level thereof, and may be set in a system memory unit (not shown) in the data processing unit 260 so that conversion is performed in the same method as in the following Table 1. The converted data is changed according to data formats shown in the following Table 2 for storage and is transmitted to a server. Regarding Tables 2 and 3 below, a real time compression process is performed on the 10-bit data given in Table 1 so that five pieces of biological data are converted into one packet. The reason why compression in Table 2 is performed is as follows. Since wireless bandwidths of a wireless network between a screening device and a smart device, and a wireless network between the smart device and a mobile communication base station may be substantially changed according to an environment, data is compressed into one packet in order to transmit and receive the data reliably. A bandwidth of datagrams shown in Table 2 is 11 bytes×200 =220 bytes/sec. As an example, a module used as a wireless communication unit uses Bluetooth 3.0 technology to transmit data to a smart device, but the exemplary embodiments are not limited thereto.

TABLE 2

| Byte order | Bit structure | Description | Notes |
| --- | --- | --- | --- |
| 1 | 0PPP PPPX | PACKET | The number of |
| 2 | 0XXX XXXX | HEADER | transmitted packets |
| 3 | 0AAA AAAA | CHANNEL 0 LSB | Target signal |
| 4 | 0BBB BBBB | CHANNEL 1 LSB | Peripheral signal 1 |
| 5 | 0AAA-BBB | CHANNEL 0 &1 MSB | Target signal and peripheral signal 1 |
| 6 | 0CCC CCCC | CHANNEL 2 LSB | Peripheral signal 2 |
| 7 | 0DDD DDDD | CHANNEL 3 LSB | Peripheral signal 3 |

TABLE 2-continued

| Byte order | Bit structure | Description | Notes |
| --- | --- | --- | --- |
| 8 | 0CCC-DDD | CHANNEL 2 &3 MSB | Peripheral signal 2 and peripheral signal 3 |
| 9 | 0EEE EEEE | CHANNEL 4 LSB | Peripheral signal 4 |
| 10 | 0FFF FFFF | CHANNEL 5 LSB | Channel 5 reserved. |
| 11 | 1EEE-FFF | CHANNEL 4 & 5 MSB | Peripheral signal 4 |

TABLE 3

| Description |
| --- |
| 1, 0: SYNC bit. MSB is set to "1" when the last byte of a packet is transmitted |
| P: 6-bit packet counter |
| X: auxiliary channel byte |
| A to F: 10-bit data value obtained through 0 to 5 channel |
| —: not used, set to "0." |

Figure 9:
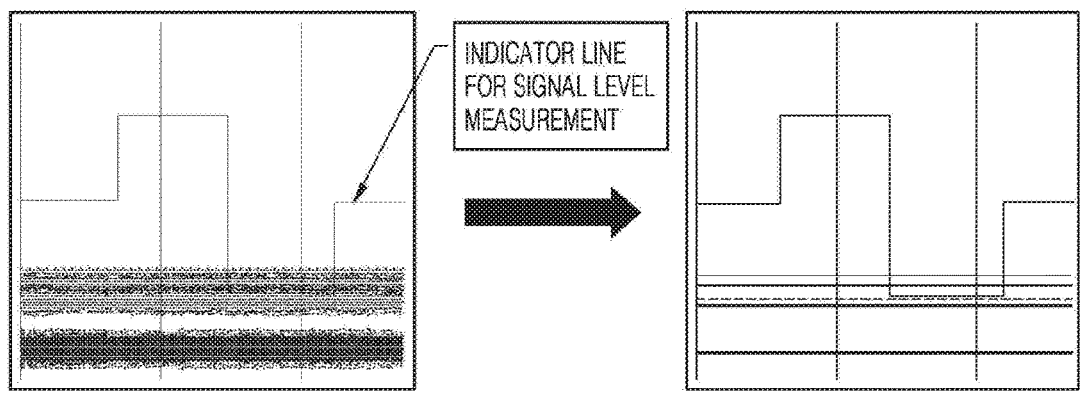
FIG. 9 is an interface screen showing a form in which a signal is processed and changed when the signal has passed a data processing unit of a portable breast cancer detection apparatus according to an exemplary embodiment.

FIG. 9 is a screen showing a form of a signal that is input to the data processing unit 260 through the AD converter and a stabilized signal that has passed through an eighth order low pass digital filter.

As shown in FIG. 9, the data converted through the AD converter 250 is transmitted to the data processing unit 260. The converted data is processed in the data processing unit 260 by a digital filter. For example, the digital filter may be implemented as software, hardware, and/or a combination thereof.

The data can be processed through the differential amplifier 220. However, in this case, there is a problem in that the size of the device increases. Therefore, according to an exemplary embodiment, the minimum number of functions that are difficult to be performed by software may be processed by hardware, and the other functions may be implemented by software. An exemplary digital filter according to an exemplary embodiment may be an eighth order low pass Chebyshev filter but the exemplary embodiments are not limited thereto. Since S3 signals that are input to the AD converter 250 through the driver amplifier 240 have widths of constant heights, when signals overlap, there is a problem in that it is difficult to determine an accurate value. When the signal passes through the filter, the signal is converted into a more simplified signal.

Figure 10:
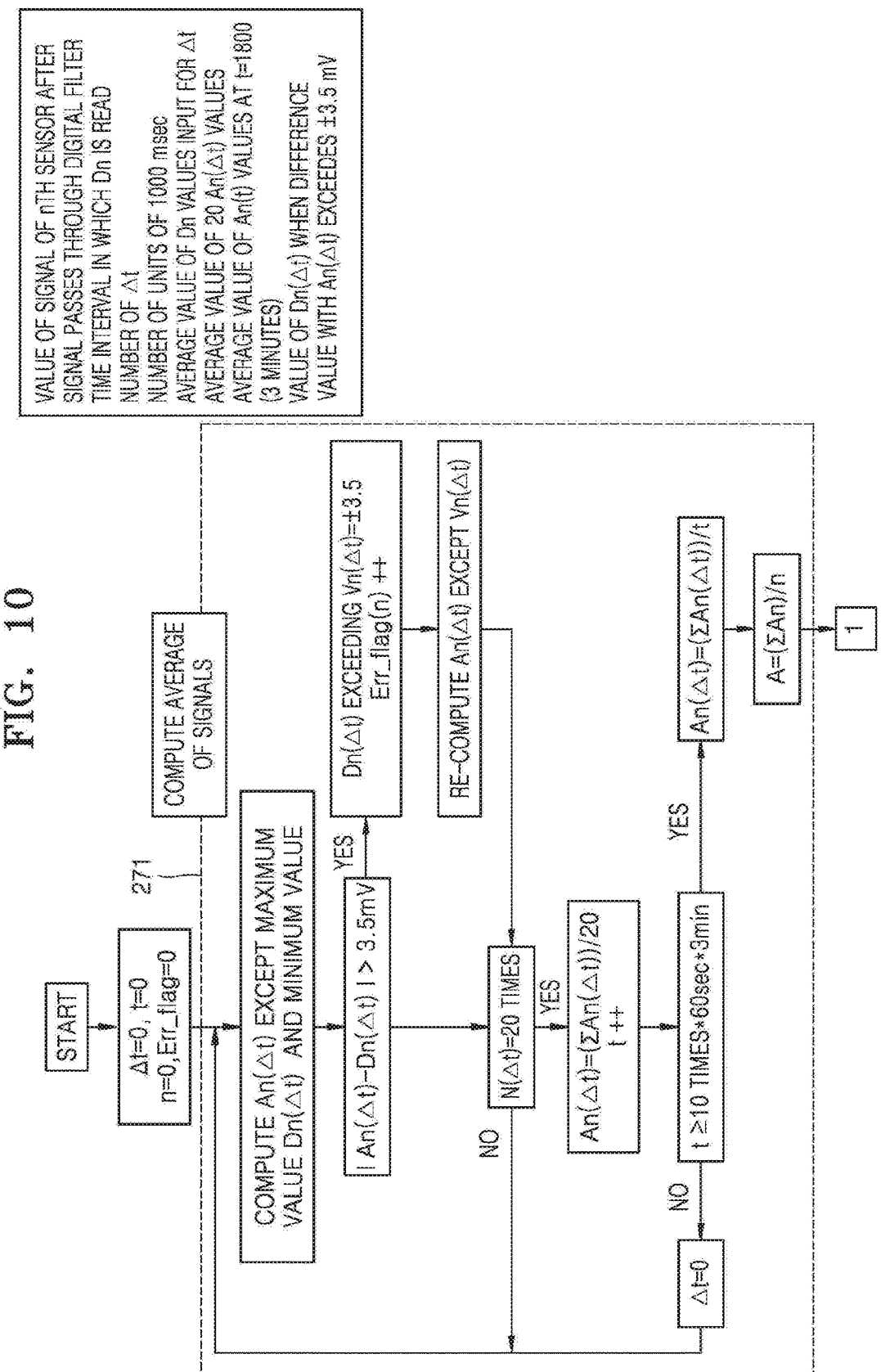
FIGS. 10 and 11 are flowcharts illustrating a process of transmitting a signal passing through a digital filter of a data processing unit to a computation unit to detect a lesion according to an exemplary embodiment.
Figure 11:
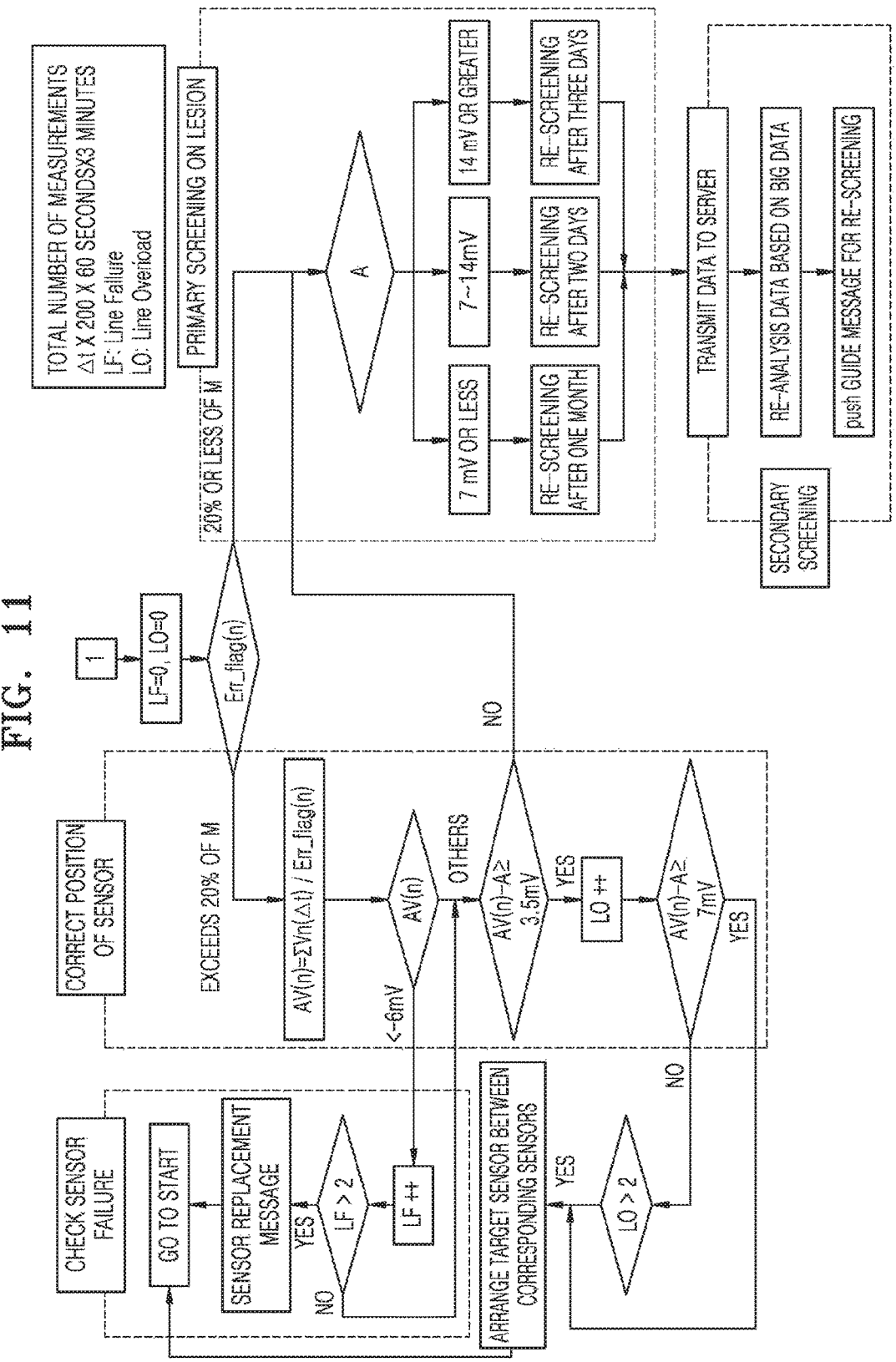
Figure 13:
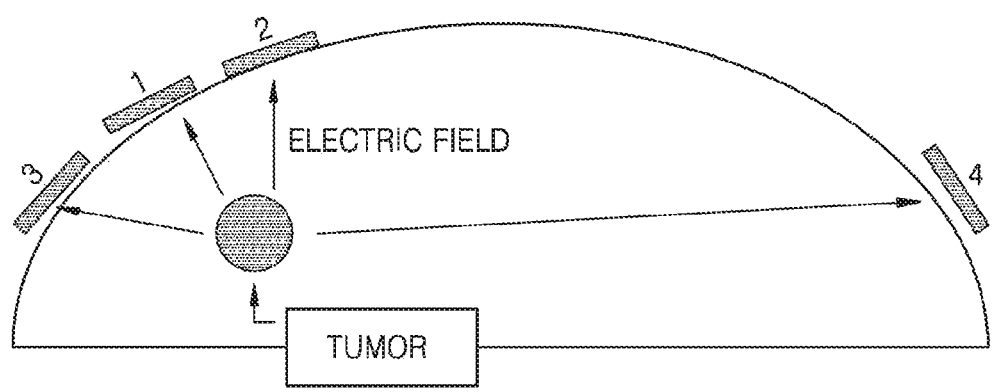

FIGS. 10 and 11 are flowcharts illustrating a process of transmitting a signal passing through a digital filter of the data processing unit 260 to a computation unit (or a controller) 270 and examining a lesion in the computation unit 270 according to an exemplary embodiment. FIGS. 12 and 13 are schematic diagrams showing processes performed by a plurality of sensor units according to an exemplary embodiment to determine a relative position with respect to a position of a malignant tumor and measure a biological signal.

Although not shown in the drawings, the computation unit 270 may include a measured value average calculation module, a sensor position correction module, a sensor failure checking module, and a lesion primary screening module (or a lesion determination controller).

Terms described in FIGS. 10 and 11 are defined as follows.

Dn: a value of a signal of an n-th sensor after the signal passes through a digital filter (for example, n=1 indicates a $1^{st}$ sensor, and n=2 indicates a $2^{nd}$ sensor)

Δt: one time interval of 5 msec during which Dn is read

N(Δt): the number of time intervals of Δt. 100 msec (or 0.1 second) when N is 20 t: the number of units of 100 msec. For example, a value of t for 3 minutes is 10×60×3=1800 times An(Δt): an average value of Dn values that are input during the time interval t An(t): an average value of 20 values of An(t)

A: an average value of An(t) values at t=1800. t=1800 indicates the number of t values for 3 minutes Vn(Δt): Dn(Δt) value when a difference from An(Δt) exceeds ±3.5 mV ++: a value of a corresponding variable is increased by one (e.g., t++: t=t+1)

Err_flag(n): the number of times an n-th sensor value exceeds a determined range. Err_flag(n) indicates whether there is a contact failure and/or whether there is a sensor failure when the number of times the n-th sensor exceeds a determined range exceeds 20% of the total number of measurements M.

M: the total number of measurements t×200×60 seconds×3 minutes

AV(n): average value of Vn values

LF: line failure

LO: line overload

In FIG. 10, an average value of values other than the maximum value and the minimum value among signal values obtained from a specific sensor unit (for example, the measurement sensor unit 110) that are sampled in the measured value average calculation module 271 is computed in the measurement sensor unit. More specifically, as shown in FIG. 9, Dn indicates a signal value in an n-th sensor after the signal passes through a digital filter. When the computation starts, an average value of the values other than the maximum value and the minimum value among a plurality of signals that are input during a time interval (t=5 msec) in which all Dn values are read at once is computed. In the following process, the process advances to the next process only when a difference between An(t), which is an average value of signals in the n-th sensor, and Dn, which is a signal value in the n-th sensor, is ±3.5 mV or less. When the difference exceeds ±3.5 mV, the value is considered to be Vn, and an average value of the Dn values other than the value is computed again. This means that, when there is a wrong input from one sensor, the input is ignored. The considered Vn value is used for an algorithm for determining whether there is a contact failure and whether there is a sensor failure in FIG. 10.

Dn is read 200 times a second and an average An(t) is computed every 20 times that Dn is read (e.g., every 100 msec). A biological signal to be measured is a signal generated when a cell is differentiated and is considered as a low speed analog signal whose state does not sharply change. A signal of 50 Hz or less may be measured in units of 10 msec. However, in an exemplary embodiment, a signal having ambiguous regularity may be sampled at least three times. In consideration of four samplings, a signal of 50 Hz or less is converted into a digital signal in 5 msec. An average of the converted signals is obtained every 20 times that a signal is converted and a change in the biological signal is appropriately traced in units of 100 msec. Therefore, An(t), which is an average value for t time interval (5 msec), is computed.

When an An(t) value is measured 20 times, An(t), which is an average value of the values, is computed. Here, the An(t) value may be interpreted as an average value of biological signals measured for 0.1 seconds. Again, 0.1 seconds is used as one unit (t) to more accurately confirm whether there is a breast cancer lesion, and an average value of An(t) values is computed to compute an average value for a time for which a screening device is attached to a subject. The portable breast cancer detecting apparatus 1000 according to an exemplary embodiment measures a biological signal of a corresponding area for, for example, 3 minutes, t=1800 is computed, and A, which is an average value of An(t) values computed every 0.1 seconds, is computed. The average value A can be used to determine whether there is a lesion.

FIG. 11 to FIG. 13 show an algorithm for interpreting data obtained by averaging and schematic diagrams for describing the same. FIGS. 12 and 13 show that, when there is a subcutaneous lesion, values of An(t) measured at skin closest thereto and in the vicinity thereof are similar.

Referring to FIG. 11, in the algorithm for determining whether there is a contact failure in a sensor and whether there is a sensor failure, when a signal value measured by a specific sensor unit (e.g., a measurement sensor unit or a peripheral sensor unit) is different from a signal value measured by the reference sensor unit 120 and an allowable range exceeding Err_flag(n), which is a value exceeding ±3.5 mV, exceeds 20% of the total number of measurements M, a position at which a sensor is attached is determined to be corrected. In this case, the position of the sensor needs to be corrected, and measurements need to be performed again.

Also, when measurement is performed as being less than a reference voltage, a Dn value exceeding ±3.5 mV based on An(t) is considered to be a Vn value and an average value of the Vn value in a time interval t is computed as AV(n). When the AV(n) value is computed to be less than −6 mV, a sensor of the sensor unit is considered to have a defect and the signal is set to be transmitted to a sensor failure checking unit. When two or more sensors within a plurality of sensor units are determined to have a value of less −6 mV, a line failure is determined, and thus a sensor replacement message may be shown.

When a difference between An(t), which is an average value for each time interval t, and a Dn value is less than ±3.5 mV, a signal may be transmitted to the lesion primary screening module to perform primary screening of a lesion. On the other hand, when the difference is ±3.5 mV or greater, it is determined that a position at which a sensor is attached needs to be corrected. In this case, to determine whether there is a line overload (LO), when a difference between AV(n), which is an average value of Vn values, and A is 7 mV or greater, the difference is determined as a line failure (LF) of a sensor and a change message is shown to suggest arranging an attached target sensor between peripheral sensors. When a difference between AV(n), which is an average value of Vn values, and A is from 3.5 to less than 7 mV and three or more sensors are determined to have a line overload, a change message may be shown to suggest arranging a target sensor between peripheral sensors. That is, when two or more sensor units are determined to be corrected, a position at which a sensor unit is attached is determined to be erroneous, and a change message may be shown to suggest changing the position of the sensor to be changed. This is based on the fact that, even when there is a lesion, the presence of the lesion may be interpreted as being at a position distanced away from a position at which a target signal is measured.

Details of determining an algorithm based on the above procedures will be described with reference to FIG. 12 and FIG. 13.

In FIG. 12, when there is a subcutaneous tumor, a first sensor 1 indicates a target signal measurement position that is closest to the tumor. Second and third sensors 2 and 3 indicate peripheral signal measurement positions. When the breast is considered to have an elliptical structure, a biological signal of a tumor can be measured in peripheral signal measurement positions in addition to the target signal measurement position, although a level of the signal may be slightly lower than that in the first sensor. However, in a fourth sensor 4, since a level of a signal of the lesion is low, it is difficult to distinguish the signal from a normal biological signal and accordingly the signal may be measured as a normal signal. When the size of the tumor increases, the tumor may be measured as being greater than a normal range of a size in the fourth sensor 4. When screening is performed while an accurate position of the lesion is not identified, it may be reasonable to exclude the minimum value of attached sensors, which is reflected in the algorithm. In consideration of the fact that the maximum value can be an instantaneous value according to characteristics of biological signals, the maximum value may also be excluded by the algorithm. For example, generation of biological signals due to activity of nerve cells at the measurement position, and generation of biological signals due to natural muscular contraction and relaxation are natural. Therefore, the maximum value and the minimum value may be excluded and the remaining signals are averaged for screening breast cancer (refer to FIG. 10)

Referring to FIGS. 12 and 13, a fifth sensor 5 (or the reference sensor unit, 120) is attached to a position symmetric to the first sensor 1 (or the measurement sensor unit, 110). In the fourth sensor 4, as the size of tumor increases in one breast (e.g., left breast), a signal is likely to be measured. However, in the fifth sensor 5, it is not easy to measure a biological signal of breast tumor of the other breast (e.g., right breast). That is, when a value of differences between the first, second, third, and fourth sensors 1-4 based on the fifth sensor 5 is calculated, there is a significant difference in the lesion. In the exemplary embodiments, the breast lesion may be screened based on this principle.

When the number of cases in which a Vn value is obtained is 20% or less of the total number of measurements (M), a primary screening may be performed on a lesion. When an average value (A) of all sensor signals is 7 mV or less, the lesion is determined to be normal, and a re-screening may be recommended a regular screening day (for example, at a one month interval). When the average value (A) is from 7 to less than 14 mV, the lesion is determined to be a tumor related to breast cancer and re-measurement is recommended after, for example, a short time (e.g., after two days) using a screening device again. When the average value (A) is measured as 14 mV or greater, the lesion is determined to be negative, and an instruction for recommending a re-screening for accurate confirmation after three days may be shown.

The data obtained as above will be summarized again as follows.

1. When a signal value measured by the measurement sensor unit 110 is the same as a signal value measured by the reference sensor unit 120, cell tissue activities of left and right breasts are the same or substantially the same.

2. When the signal value measured by the measurement sensor unit 110 is greater than the signal value measured by the reference sensor unit 120, cell tissue activity in a corresponding signal area is high.

3. Unlike case 2, when the signal value measured by the measurement sensor unit 110 is smaller, cell tissue activity is low. However, when the signal value measured by the measurement sensor unit 110 is continuously measured as being 0 at 20% or greater, the signal value is set and determined to be a contact failure in a "sensor" or a "sensor failure," and corresponding data is entirely ignored.

3-1. Further, when case 3 occurs in two or more sensor units, sensors are replaced and measurement is performed again.

3-2. When case 3 occurs again, positions of the reference sensor unit 120 and the measurement sensor unit 110 are changed and measurement is performed again.

<Basic Assumptions for Interpretation of a Breast Cancer Lesion Based on Data>

1. Left and right activities at corresponding positions on breasts having no breast cancer lesion are the same or substantially the same.

2. It is assumed that there is no probability or substantially no probability of the same lesion developing at positions that correspond to each other at left and right breasts. As discussed above, the term "positions corresponding to each other" refers to the same positions in the left breast and the right breast that have the same angle and distance from a center point of the left breast and a center point of the right breast, respectively.

3. A position of the measurement sensor unit 110 may not accurately match a position of a subcutaneous lesion.

4. A screening result is determined as being normal, requiring re-screening, or being abnormal. Values of −7 to 20 mV are divided into four groups and may be used to determine whether there is a lesion as follows. Values in parentheses below indicate decimal values.

1) 0 mV or less (0 or less): normal (however, in consideration of a possibility of a contact failure in a sensor or a sensor failure, positions of the measurement sensor unit 110 and the reference sensor unit 120 are changed and measurement is performed again)

2) 0 to 7 mV (0 to 511.5): normal 3) 7 to 14 mV (511.5 to 767.25): re-screening 4) 14 to 20 mV (767.25 to 1023): abnormal The portable breast cancer detecting apparatus 1000, shown in FIG. 5, may not include the computation unit 270. In this case, a signal that passed through a digital filter of the data processing unit 260 may be transmitted to a terminal 400 including the computation unit 270, for example, a smartphone, a computer, and a notebook, using a Bluetooth module 280, and is computed through the computation unit 270. When the apparatus 1000 include the computation unit 270, the terminal 400 still may be used to as a separate device which can share and synchronize the data with the apparatus 1000.

The signal may be transmitted to the terminal 400 through wireless communication using the wireless communication unit. The wireless communication unit may include a short-range communication module and a wireless Internet module. A wireless signal includes various formats and data according to message transmission and reception between a probe and a smart device. The wireless Internet module is a module for wireless Internet, and a WLAN, Wibro, Wimax, HSDPA, an LTE dongle, and the like may be used. The short-range communication module is a module for short-range communication. As a short-range communication technology, the Bluetooth module 280, UWB, ZigBee, and the like may be used, and particularly, a communication technology compatible with smart devices is preferentially used.

Figure 14:
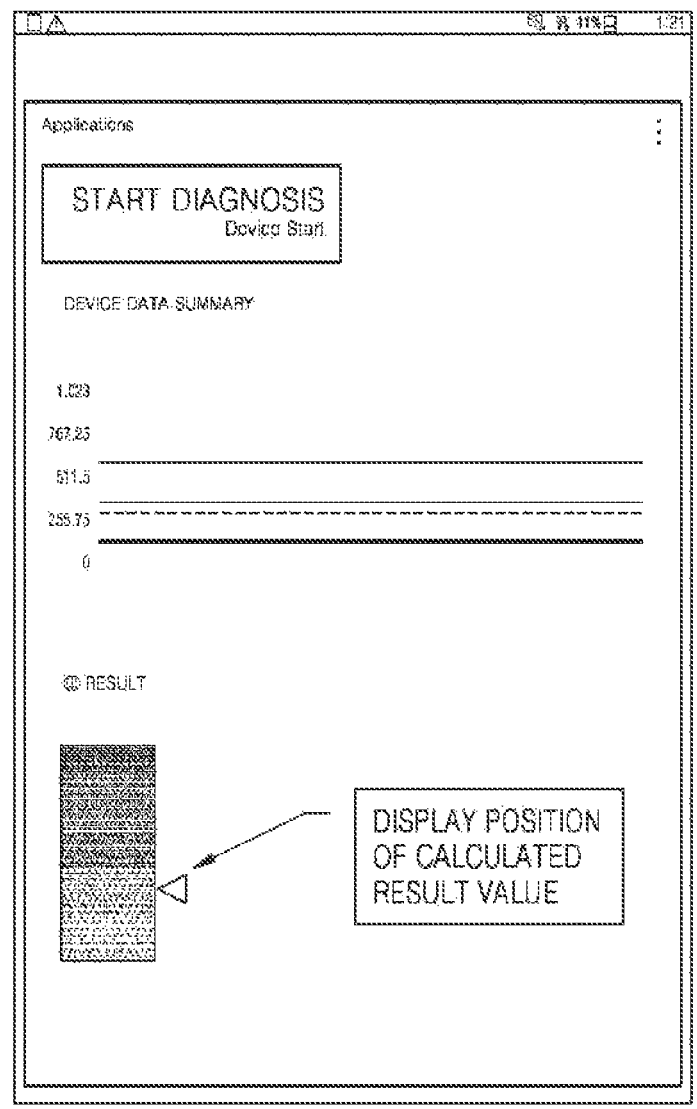
FIGS. 14 to 17 are interface screens in which a screening result of data measured by a portable breast cancer detection apparatus according to an exemplary embodiment is provided
Figure 15:
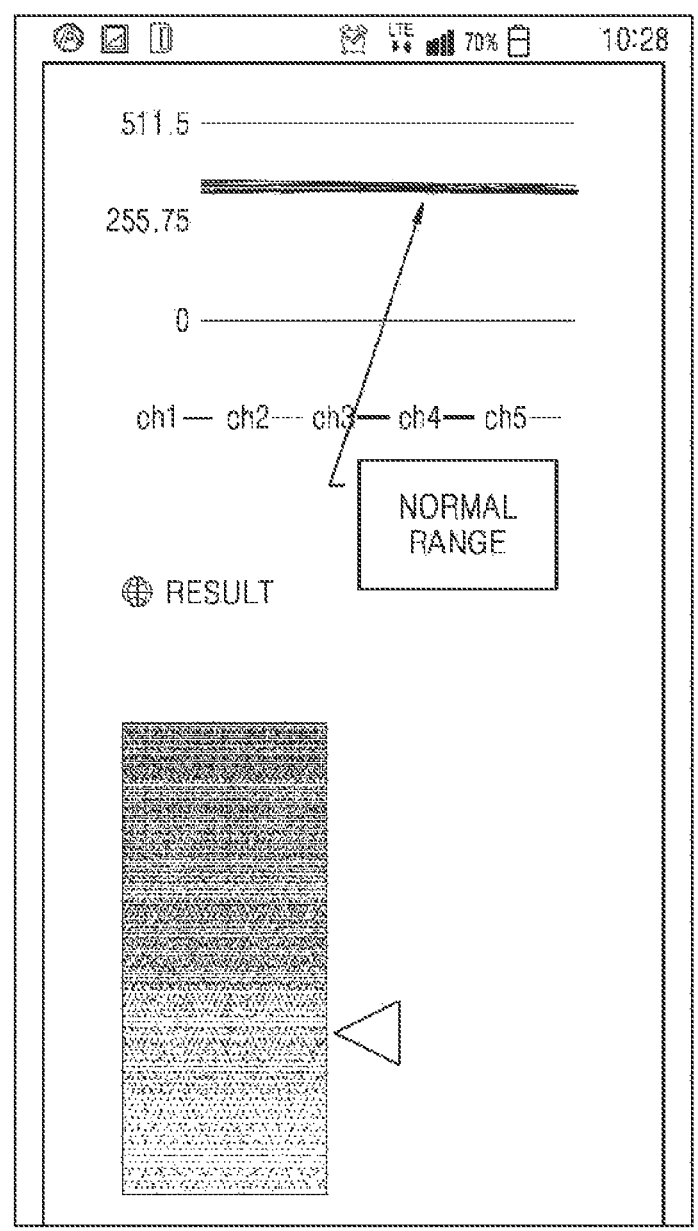
Figure 16:
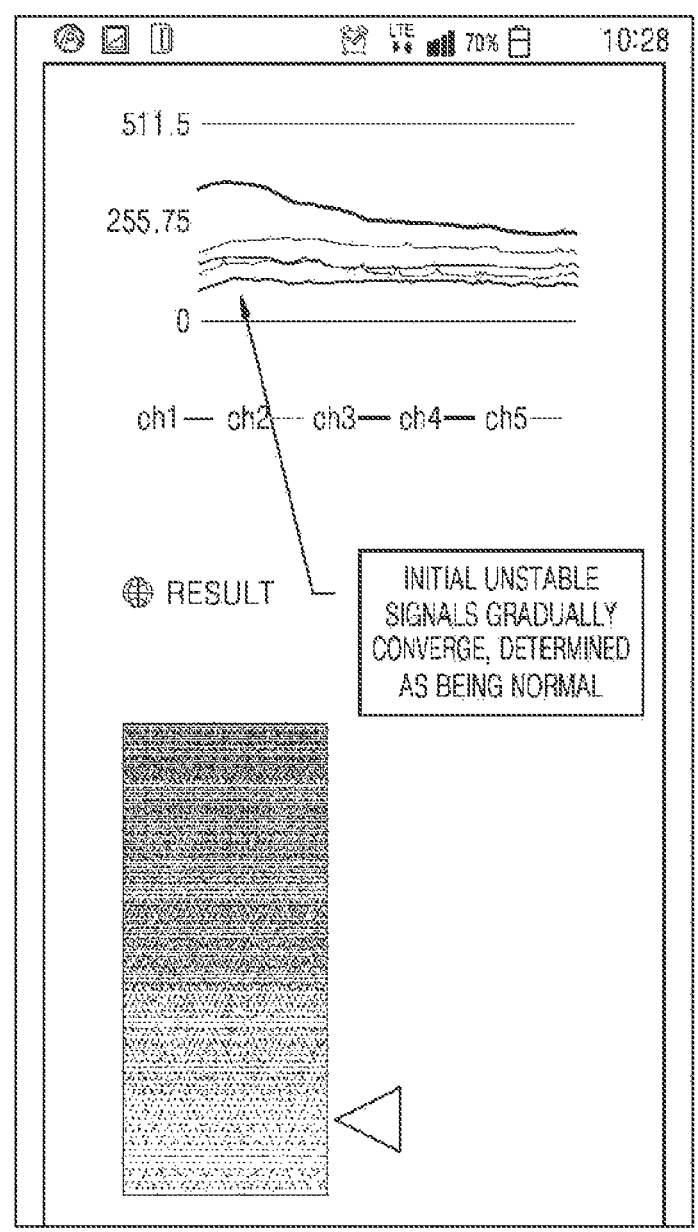
Figure 17:
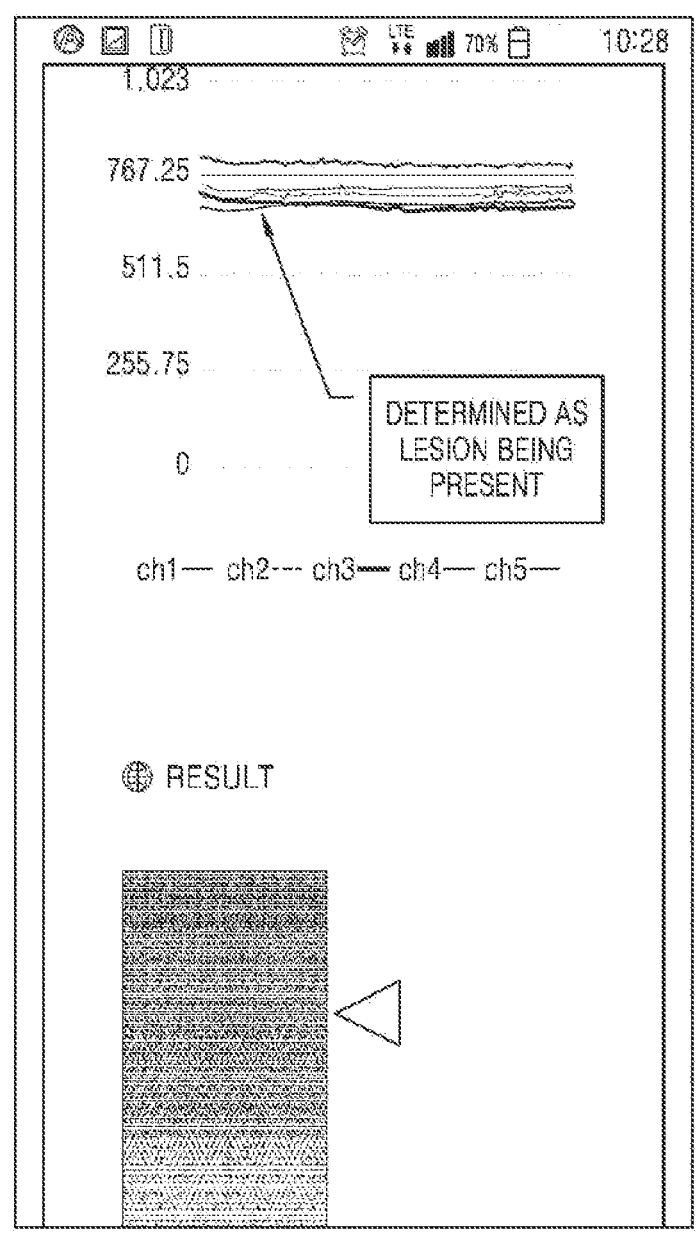

As an example, the result obtained by the portable breast cancer detecting apparatus 1000 of the exemplary embodiments can be stored and displayed through the application installed in the terminal 400. FIG. 14 to FIG. 17 show interface screens in which a screening result of data measured by the portable breast cancer detection apparatus of the exemplary embodiment is confirmed using the application. Gradient color charts can be used to interpret results values consistently. The charts show signal values obtained by the measurement sensor unit and results measured through the peripheral sensor units. An X axis represents a time and a Y axis represents data-converted biological signal values. FIG. 14 shows an interface screen before diagnosis starts. FIG. 15 to FIG. 17 are interface screens showing results values after diagnosis. FIGS. 15 and 16 show results determined as being normal. FIG. 17 shows results determined as lesion (e.g., breast cancer) being present.

In the portable breast cancer detection apparatus according to the exemplary embodiments, measurement is directly performed on a breast using one of measured signals as a reference signal instead of a right leg signal.

According to a configuration of the above device, there is no need to set a separate ground position at a human body, a distance of a measurement position is shortened, and an impedance between measured signals is decreased. Therefore, it is possible to stabilize a signal in a short time.

Also, there is no damage to a human body since the measurement method is non-invasive and screening can be performed in a short time, and the measurement method is very efficient in consideration of time and cost, precise screening of a test area is made by regulating the number of sensors, and it is possible to minimize a misdiagnosis.

At least one of the components, elements, modules or units represented by a block as illustrated in the drawings may be embodied as various numbers of hardware, software and/or firmware structures that execute respective functions described above, according to an exemplary embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the above block diagrams, communication between the components, elements or units may be performed through the bus. Functional aspects of the above exemplary embodiments may be implemented in algorithms that execute on one or more processors. Furthermore, the components, elements or units represented by a block or processing steps may employ any number of related art techniques for electronics configuration, signal processing and/or control, data processing and the like.

Although a few embodiments have been shown and described, it would be appreciated by those skilled in the art that changes may be made in exemplary embodiments without departing from the principles and spirit of the disclosure, the scope of which is defined in the claims and their equivalents.

What is claimed is:

1. A portable breast cancer screening device comprising:
    a measurement sensor configured to measure a biological potential in a first breast area of a subject;
    a reference sensor configured to measure a biological potential in a second breast area corresponding to a position at which the measurement sensor is attached; and
    a detector electrically connected to a peripheral sensor configured to measure a biological potential around the position at which the measurement sensor is attached, and configured to measure a biological potential generated in a body,
    wherein the detector comprises:
        an overvoltage/overcurrent protection circuit configured to block a leakage current from being introduced to the detector;
        a differential amplifier configured to amplify a voltage input from a sensor among the measurement sensor, the reference sensor, and the peripheral sensor;
        an active low pass filter configured to pass only a signal frequency of a low frequency band among signals transmitted from the differential amplifier;
        a driver amplifier configured to amplify a signal passed through the active low pass filter;
        an analog-to-digital (AD) converter configured to convert the signal amplified by the driver amplifier into a digital signal; and
        a ground operating circuit electrically connected to the differential amplifier,
    wherein the ground operating circuit comprises:
        an operational amplifier having two input terminals that are electrically connected to the differential amplifier and a reference voltage, respectively;
        a resistor electrically connected between the operational amplifier and an output voltage;
        a first capacitor electrically connected between the differential amplifier and the output voltage; and
        a second capacitor electrically connected between the operational amplifier and the output voltage.

2. The portable breast cancer screening device according to claim 1,
    wherein the differential amplifier is further configured to amplify a difference between two voltages when biological potential values measured by the measurement sensor and the reference sensor are input thereto.

3. The portable breast cancer screening device according to claim 1,
    wherein the differential amplifier amplifies a voltage of a difference between biological potential values measured by the peripheral sensor and the reference sensor.

4. The portable breast cancer screening device according to claim 1,
    wherein a part of the ground operating circuit is of an open loop type.

5. The portable breast cancer screening device according to claim 1,
    wherein the ground operating circuit is electrically connected to a plurality of differential amplifiers.

6. The portable breast cancer screening device according to claim 1,
    wherein the signal frequency of the low frequency band is 50 Hz or less.

7. The portable breast cancer screening device according to claim 1, further comprising:
a controller electrically connected to the AD converter and configured to store an algorithm for calculating the digital signal converted by the AD converter and confirming a breast cancer lesion.

8. The portable breast cancer screening device according to claim 7,
wherein the controller is further configured to:
measure an average value of measured sensor signals;
compute a signal value that exceeds an allowable range and determine whether to change a position at which the sensor among the measurement sensor, the reference sensor, and the peripheral sensor is attached;
determine a failure in the sensor among the measurement sensor, the reference sensor, and the peripheral sensor; and
confirm an average value of sensor signals having no error and determine whether a lesion is benign.

9. The portable breast cancer screening device according to claim 8,
wherein, when a difference between An(t), which is an average value of signals for each certain time interval (t), and a specific signal value (Dn) among a plurality of signal values input for t is equal to a specific value or greater, the controller excludes the signal value from a computation of an average value of the signals.

10. The portable breast cancer screening device according to claim 8,
wherein the controller determines whether to change the position at which the sensor among the measurement sensor, the reference sensor, and the peripheral sensor is attached when a number of sensings of a value (Vn) exceeding ±3.5 mV from an average value An(t) of signals for each certain time interval (t) is a certain ratio or higher with respect to a total number of sensings (M).

11. The portable breast cancer screening device according to claim 8,
wherein the controller determines the failure in the sensor among the measurement sensor, the reference sensor, and the peripheral sensor when a number of sensings of a value (Vn) exceeding ±3.5 mV from an average value An(t) of signals for each certain time interval (t) is a certain ratio or higher with respect to a total number of sensings (M).

12. The portable breast cancer screening device according to claim 8,
wherein the controller determines a difference of an average value (A) of all signal values measured in the sensor among the measurement sensor, the reference sensor, and the peripheral sensor to be normal when the difference is less than 7 mV, indicates suggestion of re-screening when the difference is 7 mV or greater and less than 14 mV, and determines the average value (A) to be abnormal when the difference is from 14 mV to 20 mV.

13. The portable breast cancer screening device according to claim 1, wherein the first breast area and the second breast area respectively correspond to areas on a skin of the subject.

* * * * *